United States Patent [19]
Axelsson et al.

[11] Patent Number: 5,210,091
[45] Date of Patent: May 11, 1993

[54] IMIDAZOLE COMPOUNDS AND THEIR USE

[75] Inventors: Oskar Axelsson, Malmö ; Mikkel Thaning, Hjärup, both of Sweden; Peter Moldt, Humlebaek, Denmark

[73] Assignee: NeuroSearch A/S, Glostrup, Denmark

[21] Appl. No.: 888,036

[22] Filed: May 22, 1992

Related U.S. Application Data

[63] Continuation-in-part of Ser. No. 720,021, Jun. 24, 1991, abandoned.

[51] Int. Cl.$^5$ ............... A61K 31/445; A61K 31/415; C07D 401/10; C07D 235/30
[52] U.S. Cl. .................... 514/322; 514/388; 546/199; 548/306.1; 548/307.4
[58] Field of Search ............... 548/306; 514/388, 322; 546/199

[56] References Cited

U.S. PATENT DOCUMENTS 3,989,709  11/1976  White et al. .................... 544/250
4,492,708  1/1985  Spitzer .................... 548/306

FOREIGN PATENT DOCUMENTS 5318  11/1979  European Pat. Off. .
31264  2/1991  Japan .

OTHER PUBLICATIONS

Chemical Abstracts vol. 115, Abst. 8806f (1991).

Primary Examiner—Joseph Paul Brust
Assistant Examiner—Mary Susan H. Gabilau
Attorney, Agent, or Firm—Gordon W. Hueschen

[57] ABSTRACT

The application discloses benzimidazole derivatives, pharmaceutical preparations comprised the compounds, their preparation and use in the treatment of disorders of the Central Nervous System such as ischemia, migraine, epilepsy, psychosis, Parkinsonism and depression.

10 Claims, No Drawings

IMIDAZOLE COMPOUNDS AND THEIR USE

The present application is a continuation-in-part of our prior-filed co-pending application Ser. No. 07/720,021, filed Jun. 24, 1991, now abandoned as of Jun. 11, 1992.

The present invention relates to therapeutical active compounds and their use as well as to pharmaceutical preparations comprising the compounds. The compounds of the invention possess valuable activity as calcium channel blockers which make them useful in the treatment of anoxia, ischemia, psychosis and migraine for example.

It is well known that an accumulation of calcium (calcium overload) in the brain is seen after anoxia, ischemia, migraine and other hyperactivity periods of the brain, such as after epileptic convulsions. An uncontrolled high concentration of calcium in the brain cells is known to cause most of the degenerative changes connected with above diseases. Therefore compounds which can block the calcium channels of brain cells will be useful in the treatment of anoxia, ischemia, migraine, epilepsia and in the prevention of the degenerative changes connected with the same.

Compounds blocking the socalled L-type calcium channels in the central nervous system (CNS) will be useful for the treatment of the above disorders by directly blocking the calcium uptake in the CNS.

Further, it is well known that the socalled N-type of calcium channels are involved in the regulation of the neurotransmitter release. Compounds blocking the N-type of calcium channels will indirectly and very powerfully prevent calcium overload in CNS after the hyperactivity periods of the brain as described above by inhibiting the enhanced neurotransmitter release seen after such hyperactivity, and especially the neurotoxic enhanced glutamate release after such hyperactivity periods of the CNS. Furthermore, blockers of the N-type of calcium channels will dependent upon the selectivity of the compound in question inhibit the release of various other neurotransmitters such as aspartate, GABA, glycine, dopamine, serotonin and noradrenaline and therefore blockers of N-type of calcium channels may be useful in the treatment of psychosis, Parkinsonism, depression, epilepsia and other convulsive disorders.

It is an object of the present invention to provide compounds being able to block the L-type and/or the N-type calcium channels.

The invention then, inter alia, comprises the following, alone or in combination.

A method of treating a disorder of a mammal, including a human, which is responsive to the blockade of N-type and/or L-type of calcium channels, which comprises administering to a patient in need thereof a therapeutically effective amount of a compound having the formula:

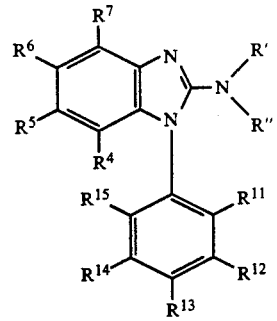

wherein
R' and R" independently are hydrogen or $C_{1-4}$-alkyl which may be straight or branched, or R' and R" together form an alkylene chain of 2–6 carbon atoms;

$R^4$, $R^5$, $R^6$, $R^7$ independently of each other are hydrogen, halogen, $CF_3$, or CN;

$R^{11}$ is hydrogen, halogen, $CF_3$, hydroxy or $OR^I$ wherein $R^I$ is $C_{1-4}$-alkyl which may be straight or branched;

$R^{12}$, $R^{13}$ and $R^{14}$ independently are hydrogen, halogen, $CF_3$, $C_{1-4}$-alkyl which may be straight or branched, OH, $OR^{16}$ wherein $R^{16}$ is $C_{1-4}$-alkyl which may be straight or branched, phenyl, piperidyl, pyrrolidyl, or phenyl which may be substituted one or more times with halogen, $CF_3$, CN, $C_{1-4}$-alkyl which may be straight or branched, OH, $NO_2$, $CO_2H$, $NH_2$, $OR^{II}$ is $C_{1-4}$-alkyl which may be straight or branched, $CO_2R^{III}$ wherein $R^{III}$ is $C_{1-4}$-alkyl which may be straight or branched, $NR^{IV}R^V$ wherein $R^{IV}$ and $R^V$ independently are hydrogen, $C_{1-6}$-alkyl which may be straight or branched, acyl, or wherein $R^{IV}$ and $R^V$ together form an alkylene chain of 2–6 carbon atoms; $R^{15}$ is hydrogen or together with $R^{14}$ form an extra benzo ring; or a pharmaceutically acceptable addition salt thereof, and the method as above wherein anoxia, ischemia, migraine, epilepsia, and the prevention of the degenerative changes connected with anoxia, ischemia, migraine, and epilepsia is treated, and the method as above wherein psychosis, Parkinsonism, depression, epilepsia or other convulsive disorders are treated, further a compound having the formula

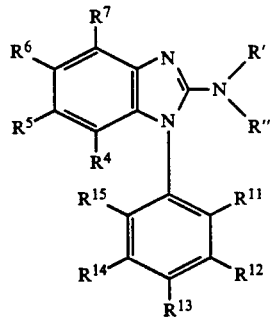

wherein
R' and R" independently are hydrogen or $C_{1-4}$-alkyl which may be straight or branched, or R' and R" together form an alkylene chain of 2–6 carbon atoms;

$R^4$, $R^5$, $R^6$ and $R^7$ independently of each other are hydrogen, halogen, $CF_3$ or CN;

$R^{11}$ is hydrogen, halogen, $CF_3$, hydroxy or $OR^I$ wherein $R^I$ is $C_{1-4}$-alkyl which may be straight or branched;

two of $R^{12}$, $R^{13}$ and $R^{14}$ independently are hydrogen, halogen, $CF_3$, $C_{1-4}$-alkyl which may be straight or branched, OH, $OR^{16}$ wherein $R^{16}$ is $C_{1-4}$-alkyl which may be straight or branched, or phenyl and the last of $R^{12}$, $R^{13}$ and $R^{14}$ is pyrrolidyl, piperidyl, or phenyl which may be substituted one or more times with halogen, $CF_3$, CN, $C_{1-4}$-alkyl which may be straight or branched, OH, $NO_2$, $CO_2H$, $NH_2$, $OR^{II}$ wherein $R^{II}$ is $C_{1-4}$-alkyl which may be straight or branched, $CO_2R^{III}$ wherein $R^{III}$ is $C_{1-4}$-alkyl which may be straight or branched, $NR^{IV}R^V$ wherein $R^{IV}$ and $R^V$ independently are hydrogen, $C_{1-6}$-alkyl which may be straight or branched, acyl, or wherein $R^{IV}$ and $R^V$ together form an alkylene chain of 2-6 carbon atoms; $R^{15}$ is hydrogen or together with $R^{14}$ form an extra benzo ring; or a pharmaceutically acceptable addition salt thereof, and a compound as above which is 1-(2-hydroxy-5-phenyl-phenyl)-2-amino-benzimidazole, and a compound as above which is 1-(2-methoxy-5-phenyl-phenyl)-2-amino-benzimidazole, and a compound as above which is 1-(2-methoxy-5-phenyl-phenyl)-2-amino-5-trifluoromethyl-benzimidazole, and a compound as above which is 1-(3-(1-piperidyl)-phenyl)-5-fluoro-2-amino-benzimidazole, still further a pharmaceutical composition comprising as active ingredient an effective amount of a compound as first above, further a method of preparing a compound having the formula

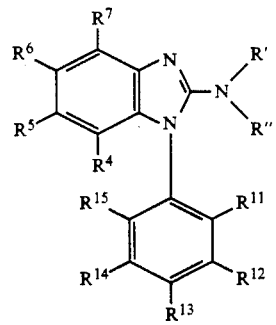

wherein

R' and R" independently are hydrogen or $C_{1-4}$-alkyl which may be straight or branched, or R' and R" together form an alkylene chain of 2-6 carbon atoms;

$R^4$, $R^5$, $R^6$ and $R^7$ independently of each other are hydrogen, halogen, $CF_3$ or CN;

$R^{11}$ is hydrogen, halogen, $CF_3$, hydroxy or $OR^I$ wherein $R^I$ is $C_{1-4}$-alkyl which may be straight or branched;

two of $R^{12}$, $R^{13}$ and $R^{14}$ independently are hydrogen, halogen, $CF_3$, $C_{1-4}$-alkyl which may be straight or branched, OH, $OR^{16}$ wherein $R^{16}$ is $C_{1-4}$-alkyl which may be straight or branched, or phenyl and the last of $R^{12}$, $R^{13}$ and $R^{14}$ is pyrrolidyl, piperidyl, or phenyl which may be substituted one or more times with halogen, $CF_3$, CN, $C_{1-4}$-alkyl which may be straight or branched, OH, $NO_2$, $CO_2H$, $NH_2$, $OR^{II}$ wherein $R^{II}$ is $C_{1-4}$-alkyl which may be straight or branched, $CO_2R^{III}$ wherein $R^{III}$ is $C_{1-4}$-alkyl which may be straight or branched, $NR^{IV}R^V$ wherein $R^{IV}$ and $R^V$ independently are hydrogen, $C_{1-6}$-alkyl which may be straight or branched, acyl, or wherein $R^{IV}$ and $R^V$ together form an alkylene chain of 2-6 carbon atoms; $R^{15}$ is hydrogen or together with $R^{14}$ form an extra benzo ring; or a pharmaceutically acceptable addition salt thereof comprising:

a) reacting a compound having the formula

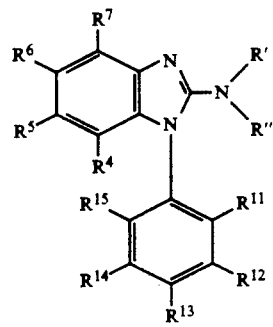

wherein

R', R", $R^4$, $R^5$, $R^6$, $R^7$, and $R^{15}$ have the meanings set forth above and wherein one of $R^{12}$, $R^{13}$ and $R^{14}$ is iodine and the other of $R^{12}$, $R^{13}$ and $R^{14}$ have the meanings set forth above, with $R^{12}$—$B(OH)_2$, $R^{13}$—$B(OH)_2$ or $R^{14}$—$B(OH)_2$, wherein $R^{12}$, $R^{13}$ and $R^{14}$ have the meanings set forth above, to form a compound of the invention, or b) reacting a compound having the formula

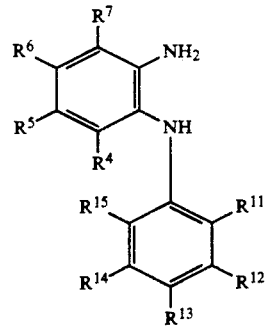

wherein $R^4$, $R^5$, $R^6$, $R^7$, $R^{11}$, $R^{12}$, $R^{13}$, $R^{14}$, and $R^{15}$ have the meanings set forth above, with cyanogen bromide, to form a compound of the invention, and the method as above wherein 1-(2-hydroxy-5-phenyl-phenyl)-2-amino-benzimidazole is prepared, and the method as above wherein 1-(2-methoxy-5-phenyl-phenyl)-2-amino-benzimidazole is prepared, and the method as above wherein 1-(2-methoxy-5-phenyl-phenyl)-2-amino-5-trifluoromethyl-benzimidazole is prepared, and the method as above wherein 1-(3-(1-piperidyl)-phenyl)-5-fluoro-2-amino-benzimidazole is prepared, as well as the use of a compound having the formula

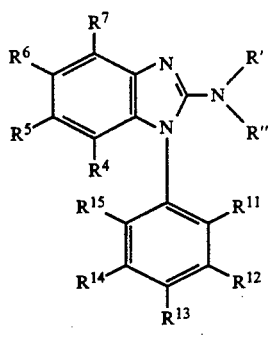

wherein

R' and R" independently are hydrogen or $C_{1-4}$-alkyl which may be straight or branched, or R' and R" together form an alkylene chain of 2–6 carbon atoms;

$R^4$, $R^5$, $R^6$, $R^7$ independently of each other are hydrogen, halogen, $CF_3$, or CN;

$R^{11}$ is hydrogen, halogen, $CF_3$, hydroxy or $OR^I$ wherein $R^I$ is $C_{1-4}$-alkyl which may be straight or branched;

$R^{12}$, $R^{13}$ and $R^{14}$ independently are hydrogen, halogen, $CF_3$, $C_{1-4}$-alkyl which may be straight or branched, OH, $OR^{16}$ wherein $R^{16}$ is $C_{1-4}$-alkyl which may be straight or branched, phenyl, piperidyl, pyrrolidyl, or phenyl which may be substituted one or more times with halogen, $CF_3$, CN, $C_{1-4}$-alkyl which may be straight or branched, OH, $NO_2$, $CO_2H$, $NH_2$, $OR^{II}$ wherein $R^{II}$ is $C_{1-4}$-alkyl which may be straight or branched, $CO_2R^{III}$ wherein $R^{III}$ is $C_{1-4}$-alkyl which may be straight or branched, $NR^{IV}R^V$ wherein $R^{IV}$ and $R^V$ independently are hydrogen, $C_{1-6}$-alkyl which may be straight or branched, acyl, or wherein $R^{IV}$ and $R^V$ together form an alkylene chain of 2–6 carbon atoms; $R^{15}$ is hydrogen or together with $R^{14}$ form an extra benzo ring; or a pharmaceutically acceptable addition salt thereof for the preparation of a medicament useful in the treatment of disorders of a mammal, including a human, responsive to the blockade of N-type and/or L-type of calcium channels, and the use of a compound having the formula,

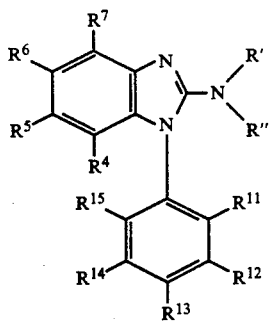

wherein

R' and R" independently are hydrogen or $C_{1-4}$-alkyl which may be straight or branched, or R' and R" together form an alkylene chain of 2–6 carbon atoms;

$R^4$, $R^5$, $R^6$, $R^7$ independently of each other are hydrogen, halogen, $CF_3$, or CN;

$R^{11}$ is hydrogen, halogen, $CF_3$, hydroxy or $OR^I$ wherein $R^I$ is $C_{1-4}$-alkyl which may be straight or branched;

$R^{12}$, $R^{13}$ and $R^{14}$ independently are hydrogen, halogen, $CF_3$, $C_{1-4}$-alkyl which may be straight or branched, OH, $OR^{16}$ wherein $R^{16}$ is $C_{1-4}$-alkyl which may be straight or branched, phenyl, piperidyl, pyrrolidyl, or phenyl which may be substituted one or more times with halogen, $CF_3$, CN, $C_{1-4}$-alkyl which may be straight or branched, OH, $NO_2$, $CO_2H$, $NH_2$, $OR^{II}$ is $C_{1-4}$-alkyl which may be straight or branched, $CO_2R^{III}$ wherein $R^{III}$ is $C_{1-4}$-alkyl which may be straight or branched, $NR^{IV}R^V$ wherein $R^{IV}$ and $R^V$ independently are hydrogen, $C_{1-6}$-alkyl which may be straight or branched, acyl, or wherein $R^{IV}$ and $R^V$ together form an alkylene chain of 2–6 carbon atoms; $R^{15}$ is hydrogen or together with $R^{14}$ form an extra benzo ring; or a pharmaceutically acceptable addition salt thereof for the preparation of a medicament useful in the treatment of anoxia, ischemia, migraine, epilepsy, psychosis, Parkinsonism depression, and the prevention of the degenerative changes connected with anoxia, ischemia, migraine and epilepsia, and the use of a compound having the formula

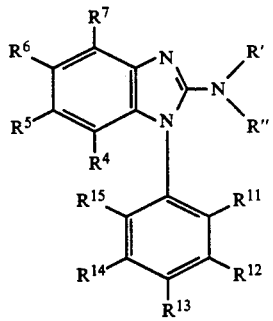

wherein

R' and R" independently are hydrogen or $C_{1-4}$-alkyl which may be straight or branched, or R' and R" together form an alkylene chain of 2–6 carbon atoms;

$R^4$, $R^5$, $R^6$ and $R^7$ independently of each other are hydrogen, halogen, $CF_3$ or CN;

$R^{11}$ is hydrogen, halogen, $CF_3$, hydroxy or $OR^I$ wherein $R^I$ is $C_{1-4}$-alkyl which may be straight or branched;

two of $R^{12}$, $R^{13}$ and $R^{14}$ independently are hydrogen, halogen, $CF_3$, $C_{1-4}$-alkyl which may be straight or branched, OH, $OR^{16}$ wherein $R^{16}$ is $C_{1-4}$-alkyl which may be straight or branched, or phenyl and the last of $R^{12}$, $R^{13}$ and $R^{14}$ is pyrrolidyl, piperidyl, or phenyl which may be substituted one or more times with halogen, $CF_3$, CN, $C_{1-4}$-alkyl which may be straight or branched, OH, $NO_2$, $CO_2H$, $NH_2$, $OR^{II}$ wherein $R^{II}$ is $C_{1-4}$-alkyl which may be straight or branched, $CO_2R^{III}$ wherein $R^{III}$ is $C_{1-4}$-alkyl which may be straight or branched, $NR^{IV}R^V$ wherein $R^{IV}$ and $R^V$ independently are hydrogen, $C_{1-6}$-alkyl which may be straight or branched, acyl, or wherein $R^{IV}$ and $R^V$ together form an alkylene chain of 2–6 carbon atoms; $R^{15}$ is hydrogen or together with $R^{14}$ form an extra benzo ring; or a pharmaceutically acceptable addition salt thereof for the preparation of a medicament useful in the treatment of disorders of a mammal, including a human, responsive to the blockade of N-type and/or L-type of calcium channels.

Examples of pharmaceutically acceptable addition salts include inorganic and organic acid addition salts such as the hydrochloride, hydrobromide, phosphate, sulphate, citrate, lactate, tartrate, maleate, fumarate, mandelate, oxalate and the acetate.

Biology

A high influx of calcium from extracelluar compartments into neurons is seen after opening of voltage operated calcium channels. Such opening of calcium channels may be induced by depolarization of neuronal membranes.

A crude synaptosome preparation contains small vesicles surrounded by neuronal membranes, and it is possible to study an opening of the voltage operated calcium channels in such a preparation.

In the below described test influx of $^{45}Ca$ into synaptosomes is studied under depolarized conditions. The effect of test substances on the depolarization induced calcium uptake can thus be studied.

Test Procedure

The cerebral cortex from a male Wistar rat is homogenized in 20 ml ice cold 0.32M saccharose. In the following steps the temperature is kept at 0° C. to 4° C. The homogenate is centrifuged at 1,000×g for 10 minutes and the supernatant recentrifuged for 20 minutes at 18,000×g. The obtained pellet is resuspended in 0.32M saccharose (10 ml per g of original tissue).

Aliquots of 0.05 ml of the hereby obtained synaptosome suspension are added to glass tubes containing 0.625 ml of a NaCl buffer (136 mM NaCl, 4 Mm KCl, 0.35 mM $CaCl_2$, 1.2 mM $MgCl_2$, 20 mM Tris HCl, 12 mM glucose, pH 7.4) as well as 0.025 ml of different test substances in 48% ethanol. These tubes are pre-incubated for 30 minutes on ice and thereafter for 6 minutes at 37° C.

$^{45}Ca$ uptake is initiated by addition to above glass-tubes of 0.4 ml $^{45}CaCl_2$ (specific activity: 29-39 Ci/g; 0.5 Ci per tube). For depolarized samples the 0.4 ml $^{45}CaCl_2$ contain KCl (145 mM) and for non-depolarized NaCl (145 mM). The samples are incubated for 15 seconds.

The $^{45}Ca$ uptake is stopped by filtering through glass fibre filters, which are subsequently washed 3 times with an ice cold solution of 145 mM KCl, 7 mM EGTA and 20 mM Tris HCl, pH 7.4 (5.0 ml). The radioactivity on the filters are measured by liquid scintillation spectrometry. Experiments are performed in duplicate.

Sample preparation

Above test substances are dissolved in for example 10 ml 48% ethanol at a concentration of 0.44 mg/ml. Dilutions are made in ethanol. Test substances are tested at concentrations of 0.1, 0.3, 1, 3, 10 . . . µg/ml.

Results

The test value is given as $IC_{50}$, that is the concentration in µM of the test substances, which inhibit 50% of the potassium stimulated uptake of $^{45}Ca$. The uptake in potassium depolarized samples are corrected for basal uptake in non-depolarized samples. The $IC_{50}$ value is determined from a dose response curve.

The results obtained by testing selected compounds according to the invention are presented in below table

TABLE

| Compound | $IC_{50}$ (µM) |
| --- | --- |
| 2-(2,5-dimethoxyphenyl)-2-amino-5-trifluoromethyl-benzimidazole | 0.7 |
| 1-(2-hydroxy-5-chlorophenyl)-5-trifluoromethyl-2-amino-benzimidazole | 2.0 |
| 1-(5-(1-pyrrolidinyl)-phenyl)-2-amino-5-fluoro-benzimidazole | 2.0 |

TABLE-continued

| Compound | $IC_{50}$ (µM) |
| --- | --- |
| fluoro-benzimidazole | |

It has been found (electrophysiological studies using the patch-clamp technique as described by Hamill et al., Pflügers Arch. 391, 85-100 (1981)), that the compounds of the invention block the N-type of calcium channels. Several compounds block the N-type calcium channels in these studies at concentrations from 0.5-10 µM. Examples of such compounds are 1-(2-hydroxy-5-phenyl-phenyl)-2-amino-5-trifluoromethyl-benzimidazole, and 1-(2-methoxy-5-phenyl-phenyl)-2-amino-5-trifluoromethyl-benzimidazole. Therefore the compounds are useful in the treatment of anoxia, ischemia and migraine (see also WO 91/07980).

Further it has been found that the compounds of the invention, for example 1-(2-hydroxy-5-phenyl-phenyl)-2-amino-benzimidazole potently antagonize hypermotility in mice as induced by amphetamine or cocaine. This is in full accordance with the influence of N-type calcium channel blockers on transmitter release in the central nervous system. Therefore the compounds of the invention are useful as anti-psychotics.

Pharmaceutical Compositions

The compounds of the invention, together with a conventional adjuvant, carrier, or diluent, may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Tablets containing ten (10) milligrams of active ingredient or, more broadly, 0.1 to one hundred (100) milligrams, per tablet, are accordingly suitable representative unit dosage forms.

Method of Treating

Due to the high degree of activity the compounds of the invention may be administered to a subject, e.g., a living animal body, in need of alleviation, treatment, or amelioration of an indication which is sensitive to the activity or influence of the compounds of the present invention including sensitive to the Ca channel blocking properties of the compounds of the invention. The compounds of the invention are preferably administered in the form of an acid addition salt thereof, concurrently, simultaneously, or together with a pharmaceutically-acceptable carrier or diluent, especially and preferably in the form of a pharmaceutical composition thereof, whether oral, rectal, or parenteral (including subcutaneous) route, in an effective amount. Suitable dosage ranges are 0.1-500 milligrams daily, preferably 1-100 milligrams daily, and especially 1-30 milligrams daily, depending as usual upon the exact mode of administration, form in which administered, the indication toward which the administration is directed, the subject involved and the body weight of the subject involved, and the preferences and experience of the physician or veterinarian in charge.

The following examples will illustrate the invention further, however they are not to be construed as limiting.

EXAMPLE 1

1-(2-Hydroxy-5-trifluoromethylphenyl)-2-amino-5-trifluoromethyl benzimidazole (1P). To a solution of 2P (4.17 g, 11.2 mmol) in a mixture of DMF and triethylamine was added cyanogen bromide (1.54 g, 14.6 mmol). The mixture was stirred for 26 h at room temperature and then diluted with water (150 ml), filtered, and neutralized with 2M aqueous sodium hydroxide. The product was filtered off and recrystallized from ethanol. Yield 430 mg, mp >360° C.

In addition to compounds 1A-1AG also 1-[1-(2-hydroxynaphtyl)]-2-aminobenzimidazole (mp 210° C.) was prepared according to example 1. The starting material in the former case was N-(2-aminophenyl)-1-amino-2-naphthol.

EXAMPLE 2

1-(2-hydroxy-5-phenyl-phenyl)-2-aminobenzimidazole (1AC). To a solution of 1H (100 mg, 0.32 mmol) in dry methylene chloride under nitrogen, was added BBr$_3$ (0.036 ml, 0.38 mmol). The mixture was stirred at room temperature for 2 h. Water was then added and the pH was adjusted to 7 by the addition of an aqueous solution of sodium carbonate. Extraction with methylene chloride and drying over MgSO$_4$ was followed by column chromatography on silica gel with methylene chloride/ethanol (25:1) as eluent.

Yield: 40 mg, 0.13 mmol, mp 259°-261° C.

EXAMPLE 3

2-Amino-4,5'-dichloro-2'-hydroxydiphenylamine (2O). A solution of 3O (6.41 g, 21.5 mmol) in a mixture of THF (100 ml) and ethanol (200 ml) was hydrogenated over 5% palladium on charcoal (500 mg) at ambient pressure until the uptake of hydrogen ceased. The mixture was filtered through celite into a flask containing 2.5 ml conc. HCl. Evaporation to dryness gave the product as a dark solid.

Yield: 6.47 g, mp 250°-280° C. (dec.).

In addition to compounds 2A-2Z also N-(2-aminophenyl)-1-amino-2-naphthol (mp 239°-246° C.) was prepared according to example 3. The starting material in the former case was N-(2-nitrophenyl)-1-amino-2-naphthol.

EXAMPLE 4

2,5-Dimethoxy-2'-nitro-4'-trifluoromethyldiphenylamine (3N). To a solution of 2,5-dimethoxy aniline (20 g, 130 mmol) in dry DMF under nitrogen, was added 80% NaH in mineral oil (4.31 g, 143 mmol). The mixture was stirred at room temperature for 1 h and then 4-chloro-3-nitrobenzotrifluoride (29.45 g, 130 mmol) was added. After stirring overnight at room temperature the excess sodium hydride was destroyed by the addition of a small amount of water. Dilution with 0.3M aqueous HCl gave a crystalline product which was filtered off and washed, first with water and then with petroleum ether. The product was dissolved in methylene chloride and filtered through a short column of silica gel. After evaporation of the solvent an orange coloured crystalline solid remained.

Yield 15.33 g, mp 93°-95° C.

In addition to compounds 3A-3Z also N-(2-nitrophenyl)-1-amino-2-naphthol (mp 185°-188° C.) was prepared according to example 3. The starting material in the former case was 3-(2-nitrophenyl)benzo[e]benzoxazole-2-one.

EXAMPLE 5

4,5'-Bistrifluoromethyl-2'-hydroxy-2-nitrodiphenylamine (3P). To a solution of 4E (5.0 g, 12.75 mmol) in dimethoxy ethane was added 38.25 ml 1M aqueous NaOH. The mixture was stirred overnight. Dilution with water and neutralization with 1M HCl was followed by extraction with ether. Evaporation at room temperature gave an orange coloured oil that crystallized upon storage in the freezer.

Yield: 4.01 g, mp 120°-123° C.

EXAMPLE 6

1-(2-Methoxy-5-chlorophenyl)-2-dimethylamino-5-trifluoromethylbenzimidazole. To a solution of 1Q (0.5 g, 1.37 mmol) in ethanol was added K$_2$CO$_3$ (0.38 g, 2.74 mmol) and iodometane (1.94 g, 13.7 mmol). The mixture was refluxed for 20 h, filtered, and evaporated to dryness. The product was purified by chromatography on silica gel with methylene chloride/methanol (9:1) as eluent. Yield 50 mg, mp 230°-234° C.

TABLE 1

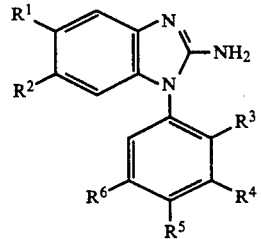

| No | R1 | R2 | R3 | R4 | R5 | R6 | Mp/°C. | Starting Material |
|---|---|---|---|---|---|---|---|---|
| 1A | H | H | OCH$_3$ | H | H | Cl | 207–208 | 2A |
| 1B | CF$_3$ | H | OH | H | H | H | 190–195 | 2B |
| 1C | CF$_3$ | H | OCH$_3$ | H | H | Ph | 227–231 | 2C |
| 1D | Cl | Cl | OCH$_3$ | H | H | Cl | 222–224 | 2D |
| 1E | CF$_3$ | H | H | CF$_3$ | H | H | 174–175 | 2E |
| 1F | CF$_3$ | H | H | OCH$_3$ | H | CF$_3$ | 194–195 | 2F |
| 1G | CN | H | OH | H | H | Cl | 250–254 | 2G |
| 1H | H | H | OCH$_3$ | H | H | Ph | 234–238 | 2H |
| 1I | CF$_3$ | H | OCH$_3$ | H | H | CF$_3$ | 214–217 | 2I |
| 1J | CF$_3$ | H | H | Cl | H | H | 221–224 | 2J |
| 1K | CF$_3$ | H | OCH$_3$ | H | H | CH$_3$ | 210–212 | 2K |
| 1L | H | H | OH | H | H | Cl | 276–278 | 2L |
| 1M | CF$_3$ | H | OCH$_3$ | H | H | F | 180–184 | 2M |
| 1N | CF$_3$ | H | OCH$_3$ | H | H | OCH$_3$ | 192–194 | 2N |
| 1O | Cl | H | OH | H | H | Cl | 286– | 2O |

TABLE 1-continued

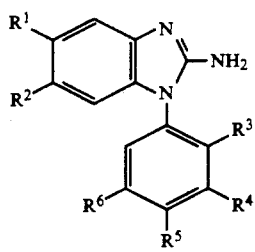

| No | R1 | R2 | R3 | R4 | R5 | R6 | Mp/°C. | Starting Material |
|---|---|---|---|---|---|---|---|---|
| 1P | CF₃ | H | OH | H | H | CF₃ | 288->360 | 2P |
| 1Q | CF₃ | H | OH | H | H | Cl | 292-293 | 2Q |
| 1R | CF₃ | H | H | H | CF₃ | H | 220-222 | 2R |
| 1S | CF₃ | H | CF₃ | H | H | H | 201-204 | 2S |
| 1T | CF₃ | H | H | Cl | Cl | Cl | 208-210 | 2T |
| 1U | CF₃ | H | H | CF₃ | Cl | H | 213-215 | 2U |
| 1V | CF₃ | H | H | I | H | H | 190-193 | 2V |
| 1W | CF₃ | H | H | 1-pyr. | H | H | 239-241 | 2W |
| 1X | CF₃ | H | H | H | OPh | H | 58-63 | 2X |
| 1Y | F | H | H | 1-pip. | H | H | 151-153 | 2Y |
| 1Z | CF₃ | H | H | OPh | H | H | 177-179 | 2Z |
| 1AA | Cl | Cl | OH | H | H | Cl | >360 | 1D |
| 1AB | CF₃ | H | H | H | H | CH₃ | 202-206 | 1F |
| 1AC | H | H | OH | H | H | Ph | 259-261 | 1H |
| 1AD | CF₃ | H | OH | H | H | CH₃ | 278-281 | 1K |
| 1AF | CF₃ | H | OH | H | H | F | 230-232 | 1M |
| 1AG | CF₃ | H | OH | H | H | OH | 149-151 | 1N |

1-pyr. = 1-pyrrolidino.
1-pip. = 1-piperidino.
Compounds 1A-1Z were prepared according to example 1 and compounds 1AA-1AG according to example 2.

TABLE 2

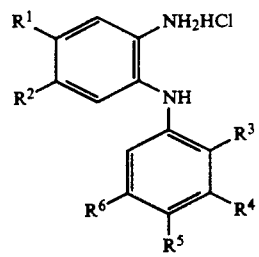

| No | R¹ | R² | R³ | R⁴ | R⁵ | R⁶ | mp/°C. | Starting material |
|---|---|---|---|---|---|---|---|---|
| 2A | H | H | OCH₃ | H | H | Cl | 156-168 (d) | 3A |
| 2B | CF₃ | H | OH | H | H | H | 200-220 (d) | 3B |
| 2C | CF₃ | H | OCH₃ | H | H | Ph | 181-184 | 3C |
| 2D | Cl | Cl | OCH₃ | H | H | Cl | 174-176 | 3D |
| 2E | CF₃ | H | H | CF₃ | H | H | 184-186 | 3E |
| 2F | CF₃ | H | H | OCH₃ | H | CF₃ | 167-169 | 3F |
| 2G | CN | H | OH | H | H | Cl | 170-172 | 3G |
| 2H | H | H | OCH₃ | H | H | Ph | 127-150 (d) | 3H |
| 2I | CF₃ | H | OCH₃ | H | H | CF₃ | 177-180 | 3I |
| 2J | CF₃ | H | H | Cl | H | H | 182-184 | 3J |
| 2K | CF₃ | H | OCH₃ | H | H | CH₃ | 148-151 | 3K |
| 2L | H | H | OH | H | H | Cl | 245 (d) | 3L |
| 2M | CF₃ | H | OCH₃ | H | H | F | 182-184 | 3M |
| 2N | CF₃ | H | OCH₃ | H | H | OCH₃ | 156-160 | 3N |
| 2O | Cl | H | OH | H | H | Cl | 250-280 | 3O |
| 2P | CF₃ | H | OH | H | H | CF₃ | 200-205 | 3P |
| 2Q | CF₃ | H | OH | H | H | Cl | 202-207 | 3Q |
| 2R | CF₃ | H | H | H | CF₃ | H | 163-165 | 3R |
| 2S | CF₃ | H | CF₃ | H | H | H | 78-80 | 3S |
| 2T | CF₃ | H | H | Cl | Cl | Cl | 216-218 | 3T |
| 2U | CF₃ | H | H | CF₃ | Cl | H | 184-186 | 3U |
| 2V | CF₃ | H | H | I | H | H | 182-185 | 3V |
| 2W | CF₃ | H | H | 1-pyr. | H | H | 210 (d) | 3W |
| 2X | CF₃ | H | H | H | OPh | H | * | 3X |
| 2Y | F | H | H | 1-pip. | H | H | 220 (d) | 3Y |
| 2Z | CF₃ | H | H | OPh | H | H | 180-183 | 3Z |

1-pyr. = 1-pyrrolidyl.
1-pip. = 1-piperidyl.
* = Isolated in an impure state unsuitable for melting point determination.

TABLE 3

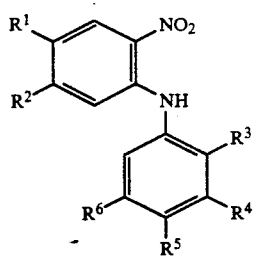

| No | R¹ | R² | R³ | R⁴ | R⁵ | R⁶ | mp/°C. | Starting material |
|---|---|---|---|---|---|---|---|---|
| 3A | H | H | OCH₃ | H | H | Cl | 112–113 | c |
| 3B | CF₃ | H | OH | H | H | H | * | 4A |
| 3C | CF₃ | H | OCH₃ | H | H | Ph | * | c |
| 3D | Cl | Cl | OCH₃ | H | H | Cl | * | c |
| 3E | CF₃ | H | H | CF₃ | H | H | 80–82 | c |
| 3F | CF₃ | H | H | OCH₃ | H | CF₃ | 94–96 | c |
| 3G | CN | H | OH | H | H | Cl | 210–212 | 4B |
| 3H | H | H | OCH₃ | H | H | Ph | oil | c |
| 3I | CF₃ | H | OCH₃ | H | H | CF₃ | 86–88 | c |
| 3J | CF₃ | H | H | Cl | H | H | 92–94 | c |
| 3K | CF₃ | H | OCH₃ | H | H | CH₃ | 106–109 | c |
| 3L | H | H | OH | H | H | Cl | 156–158 | 4C |
| 3M | CF₃ | H | OCH₃ | H | H | F | 131–134 | c |
| 3N | CF₃ | H | OCH₃ | H | H | OCH₃ | 93–95 | c |
| 3O | Cl | H | OH | H | H | Cl | 199–203 | 4D |
| 3P | CF₃ | H | OH | H | H | CF₃ | 120–123 | 4E |
| 3Q | CF₃ | H | OH | H | H | Cl | 179–181 | 4F |
| 3R | CF₃ | H | H | H | CF₃ | H | 67–69 | c |
| 3S | CF₃ | H | CF₃ | H | H | H | 87–89 | c |
| 3T | CF₃ | H | H | Cl | Cl | Cl | 137–140 | c |
| 3U | CF₃ | H | H | CF₃ | Cl | H | 93–94 | c |
| 3V | CF₃ | H | H | I | H | H | 98–101 | c |
| 3W | CF₃ | H | H | 1-pyr. | H | H | oil | c |
| 3X | CF₃ | H | H | H | OPh | H | 94–96 | c |
| 3Y | F | H | H | 1-pip. | H | H | oil | c |
| 3Z | CF₃ | H | H | OPh | H | H | oil | c |

1-pyr. = 1-pyrrolidyl.
1-pip. = 1-piperidyl.
* = Isolated in an impure state unsuitable for melting point determination.
c = Prepared from commercially available or know anilines and 2-halo-1-nitrobenzenes.

TABLE 4

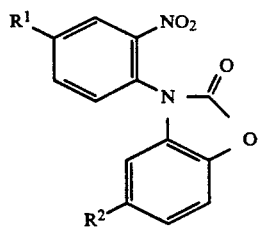

| No. | R¹ | R² | mp/°C. |
|---|---|---|---|
| 4A | CF₃ | H | * |
| 4B | CN | Cl | 228–230 |
| 4C | H | Cl | 121–123 |
| 4D | Cl | Cl | 172–174 |
| 4E | CF₃ | CF₃ | 154–156 |

TABLE 4-continued

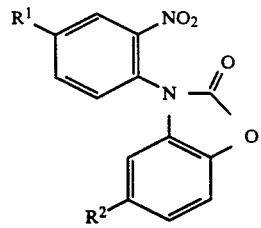

| No. | R¹ | R² | mp/°C. |
|---|---|---|---|
| 4F | CF3 | Cl | 177–180 |

* = Isolated in an impure state unsuitable for melting point determination.

We claim:

1. A method of treating a disorder of a mammal, including a human, which is responsive to the blockade of N-type and/or L-type of calcium channels, which comprises administering to a patient in need thereof a therapeutically effective amount of a compound having the formula:

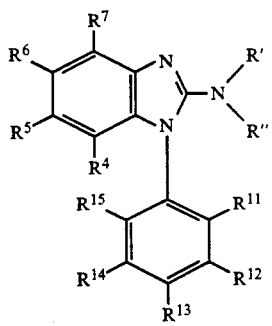

wherein
R' and R" independently are hydrogen or $C_{1-4}$-alkyl which may be straight or branched, or R' and R" together form an alkylene chain of 2–6 carbon atoms;

$R^4$, $R^5$, $R^6$, $R^7$ independently of each other are hydrogen, halogen, $CF_3$, or CN;

$R^{11}$ is hydrogen, halogen, $CF_3$, hydroxy or $OR^I$ wherein $R^I$ is $C_{1-4}$-alkyl which may be straight or branched;

$R^{12}$, $R^{13}$ and $R^{14}$ independently are hydrogen, halogen, $CF_3$, $C_{1-4}$-alkyl which may be straight or branched, OH, $OR^{16}$ wherein $R^{16}$ is $C_{1-4}$-alkyl which may be straight or branched, phenyl, piperidyl, pyrrolidyl, or phenyl which may be substituted one or more times with halogen, $CF_3$, CN, $C_{1-4}$-alkyl which may be straight or branched, OH, $NO_2$, $CO_2H$, $NH_2$, $OR^{II}$ wherein $R^{II}$ is $C_{1-4}$-alkyl which may be straight or branched, $CO_2R^{III}$ wherein $R^{III}$ is $C_{1-4}$-alkyl which may be straight or branched, $NR^{IV}R^V$ wherein $R^{IV}$ and $R^V$ independently are hydrogen, $C_{1-6}$-alkyl which may be straight or branched, acyl, or wherein $R^{IV}$ and $R^V$ together form an alkylene chain of 2–6 carbon atoms; $R^{15}$ is hydrogen or together with $R^{14}$ form an extra benzo ring; or a pharmaceutically acceptable addition salt thereof.

2. The method of claim 1 wherein anoxia, ischemia, migraine, epilepsia, and the prefention of the degenerative changes connected with anoxia, ischemia, migraine, and epilepsia is treated.

3. The method of claim 1 wherein psychosis, Parkinsonism, depression, epilepsia or other convulsive disorders are treated.

4. A compound having the formula

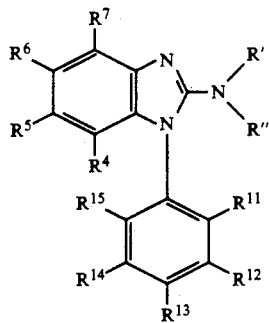

wherein
- R' and R" independently are hydrogen or $C_{1-4}$-alkyl which may be straight or branched, or R' and R" together form an alkylene chain of 2-6 carbon atoms;
- $R^4$, $R^5$, $R^6$ and $R^7$ independently of each other are hydrogen, halogen, $CF_3$ or CN;
- $R^{11}$ is hydrogen, halogen, $CF_3$, hydroxy or $OR^I$ wherein $R^I$ is $C_{1-4}$-alkyl which may be straight or branched;
- two of $R^{12}$, $R^{13}$ and $R^{14}$ independently are hydrogen, halogen, $CF_3$, $C_{1-4}$-alkyl which may be straight or branched, OH, $OR^{16}$ wherein $R^{16}$ is $C_{1-4}$alkyl which may be straight or branched, or phenyl and the last of $R^{12}$, $R^{13}$ and $R^{14}$ is pyrrolidyl, piperidyl, or phenyl which may be substituted one or more times with halogen, $CF_3$, CN, $C_{1-4}$-alkyl which may be straight or branched, OH, $NO_2$, $CO_2H$, $NH_2$, $OR^{II}$ wherein $R^{II}$ is $C_{1-4}$-alkyl which may be straight or branched, $CO_2R^{III}$ wherein $R^{III}$ is $C_{1-4}$-alkyl which may be straight or branched, $NR^{IV}R^V$ wherein $R^{IV}$ and $R^V$ independently are hydrogen, $C_{1-6}$-alkyl which may be straight or branched, acyl, or wherein $R^{IV}$ and $R^V$ together form an alkylene chain of 2-6 carbon atoms; $R^{15}$ is hydrogen or together with $R^{14}$ form an extra benzo ring; or a pharmaceutically acceptable addition salt thereof.

5. A compound of claim 4 which is 1-(2-hydroxy-5-phenyl-phenyl)-2-amino-benzimidazole.

6. A compound of claim 4 which is 1-(2-methoxy-5-phenyl-phenyl)-2-amino-benzimidazole.

7. A compound of claim 4 which is 1-(2-methoxy-5-phenyl-phenyl)-2-amino-5-trifluoromethyl-benzimidazole.

8. A compound of claim 4 which is 1-(3-(1-piperidyl)-phenyl)-5-fluoro-2-amino-benzimidazole.

9. A pharmaceutical composition comprising as active ingredient an effective amount of a compound of claim 4 together with a pharmaceutically-acceptable carrier or diluent.

10. A method of claim 1 wherein the compound is administered in the form of a pharmaceutical composition in which it is present together with a pharmaceutically-acceptable carrier or diluent.

* * * * *

UNITED STATES PATENT AND TRADEMARK OFFICE
CERTIFICATE OF CORRECTION

PATENT NO. : 5,210,091

DATED : May 11, 1993

INVENTOR(S) : Oskar Axelsson, Mikkel Thaning, Peter Moldt

It is certified that error appears in the above-identified patent and that said Letters Patent is hereby corrected as shown below:

Title page, Item [56]      Assistant Examiner--;
    "Gabilau" should read --Gabilan--.
Column 2, line 31; "$OR^{II}$ is" should read  --$OR^{II}$ wherein
    $R^{II}$ is --.
Column 6, line 7; "$OR^{II}$ is"  should read --$OR^{II}$ wherein
    $R^{II}$ is --.
Column 10, TABLE I, in the table, column heading Mp/°C.,
    last entry; "286-" should read -- 286-288--.
Column 11, TABLE I-continued, in the table, column heading
    Mp/°C., first entry; delete "288".
Column 14, line 66; "prefention" should read --prevention--.

Signed and Sealed this

Twelfth Day of April, 1994

Attest:

BRUCE LEHMAN

Attesting Officer

*Commissioner of Patents and Trademarks*